United States Patent [19]

Talaga et al.

[11] Patent Number: 5,326,875
[45] Date of Patent: Jul. 5, 1994

[54] ALKYLATION OF AZAGLYCINE DERIVATIVES

[75] Inventors: Patrice Talaga, Brussels, Belgium; Wolfgang König, Hofheim am Taunus, Fed. Rep. of Germany

[73] Assignee: Hoechst Aktiengesellschaft, Frankfurt am Main, Fed. Rep. of Germany

[21] Appl. No.: 822,929

[22] Filed: Jan. 21, 1992

[30] Foreign Application Priority Data

Jan. 24, 1991 [DE] Fed. Rep. of Germany ....... 4102015

[51] Int. Cl.$^5$ ............................................ C07C 281/06
[52] U.S. Cl. .................................... 546/332; 548/531; 560/34
[58] Field of Search ................ 546/336, 332; 548/531; 560/34

[56] References Cited

PUBLICATIONS

T. Kolasa et al. Oxidations of Some Alpha-Amino Acids Under Mitsunobu Reaction Conditions, Tetrahedron Letters, Bd. 29, Nr. 37, 1988 pp. 4661–4664.
European Search Report EP 92 10 1078, dated Apr. 14, 1992.
The Use of Diethyl Azolicarboxylate and Triphenylphosphine in Synthesis and Transformation of Natural Products, O. Mitsunobu, Synthesis 1981.
Synthesis of N-Acyl-, N-Sulfonyl-, and N-Phosphinylphospha-λ$^5$-azenes by a Redox-Condensation Reaction Using Amides, Triphenylphosphine, and Diethyl Azodicarboxylate, Bittner et al., J. Orig. Chem. 1985, vol. 50, pp. 1712–1718.

Primary Examiner—C. Warren Ivy
Assistant Examiner—Zinna N. Davis
Attorney, Agent, or Firm—Finnegan, Henderson, Farabow, Garrett & Dunner

[57] ABSTRACT

A process for the preparation of alkylated azaglycine derivatives of the formula I $$X-(A)_n-N(R)-NH-CO-NH_2, \qquad (I)$$

is described in which X is an amino protective group, $C_1$–$C_8$-alkanoyl, $C_6$–$C_{14}$-arylcarbonyl or $C_6$–$C_{14}$-aryl-$C_1$–$C_4$-alkanoyl, A is amino acid or imino acid radicals optionally protected on the third function, n is 0–10, X being $C_1$–$C_8$-alkanoyl, $C_6$–$C_{14}$-arylcarbonyl or $C_6$–$C_{14}$-aryl-$C_1$–$C_4$-alkanoyl if n=0, and R is $C_1$–$C_8$-alkyl, $C_6$–$C_{14}$-aryl-$C_1$–$C_4$-alkanoyl or $C_5$–$C_{12}$-heteroaryl-$C_1$–$C_4$-alkanoyl, which comprises reacting a compound of the formula $X-(A)_n-NH-NH-CO-NH_2$, in which X, A and n have the abovementioned meanings, with a primary or secondary alcohol and excess DEAD, and a tri-$C_1$–$C_6$-alkylphosphine, tri-$C_6$–$C_{14}$-arylphosphine or pyridyl-di-$C_6$–$C_{14}$-arylphosphine, it being possible for the aryl moiety to be optionally substituted by di-$C_1$–$C_4$-alkylamino, in an ether at 0° C. to 30° C. and optionally removing the amino protective group X, with the proviso that X is not Fmoc when tri-n-butylphosphine is used.

2 Claims, No Drawings

ALKYLATION OF AZAGLYCINE DERIVATIVES

DESCRIPTION

The redox condensation system diethyl azodicarboxylate (DEAD) - triphenylphosphine (TPP), better known as the Mitsunobu system, is a very popular method for carrying out alkylation reactions (for example on imides, heterocyclic structures etc.) (O. Mitsunobu, Synthesis 1981, 1). However, primary and secondary amides cannot be alkylated using this system (S. Bittner et al., J. Org. Chem. 1985, 50, 1712).

Surprisingly, we found that acylated azaglycine derivatives can be alkylated using the Mitsunobu reaction.

The invention therefore relates to a process for the preparation of alkylated azaglycine derivatives of the formula I

in which
X is an amino protective group, $C_1$–$C_8$-alkanoyl, $C_6$–$C_{14}$-arylcarbonyl or $C_6$–$C_{14}$-aryl-$C_1$–$C_4$-alkanoyl,
A is amino acid or imino acid radicals optionally protected on the third function,
n is 0–10, preferably 1–5, X being $C_1$–$C_8$-alkanoyl, $C_6$–$C_{14}$-arylcarbonyl or $C_6$–$C_{14}$-aryl-$C_1$–$C_4$-alkanoyl if n=0, and
R is $C_1$–$C_8$-alkyl, $C_6$–$C_{14}$-aryl-$C_1$–$C_4$-alkanoyl or $C_5$–$C_{12}$-heteroaryl-$C_1$–$C_4$-alkanoyl,
which comprises reacting a compound of the general formula II

in which X, A and n have the abovementioned meanings, with a primary or secondary alcohol and excess DEAD, preferably about 3 equivalents, and a tri-$C_1$–$C_6$-alkylphosphine, tri-$C_6$–$C_{14}$-arylphosphine or pyridyl-di-$C_6$–$C_{14}$-arylphosphine, it being possible for the aryl moiety to be optionally substituted by di-$C_1$–$C_4$-alkylamino, in an ether at 0° C. to 30° C. and removing the amino protective group X, if appropriate by the generally known methods, with the proviso that X is not Fmoc when tri-n-butylphosphine is used.

Among the phosphine derivatives, triphenylphosphine, tri-n-butylphosphine, p-dimethylaminophenyldiphenylphosphine (M. von Itzstein et al., Synth. Comm. 1990, 20, 2049), pyridyldiphenylphosphine (Ibid), and polymer-bound triphenylphosphine (R. A. Amos, J. Org. Chem. 1983, 48, 3598), in particular triphenylphosphine, are preferably used.

The alcohols used for alkylation are preferably primary and secondary $C_1$–$C_{18}$-alkylalkanols, such as, for example, methanol, ethanol, $C_6$–$C_{14}$-aryl-$C_1$–$C_4$-alkanol, such as, for example, benzyl alcohol, naphthyl-$C_1$–$C_4$-alkanol, or $C_5$–$C_7$-heteroaryl alcohols, such as, for example, pyridyl-$C_1$–$C_7$-alkanol, it being possible for the aryl and heteroaryl alcohols also to be substituted in the aromatic ring by halogen, such as fluorine, chlorine, bromine or iodine, $C_1$–$C_6$-alkyl or $C_1$–$C_6$-alkoxy.

An amino acid as mentioned above is any natural or unnatural amino acid which, if chiral, is present in the D- or L-form. α-Amino acids are preferred. Examples which may be mentioned are: Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)₂, Cyta, Daad, Dab, Dadd, Dap, Dapm, Dasu, Djen, Dpa, Dtc, Fel, Gln, Glu, Gly, Guy, hAla, hArg, hCys, hGln, hGlu, His, hIle, hLeu, hLys, hMet, hPro, hPhe, hSer, hThr, hTrp, hTyr, Hyl, Hyp, 3Hyp, Ils, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tly, Tia, Tle, Trp, Trta, Tyr, Val, Nal, Tbg, Npg, Chg, Cha, Thia (cf., for example, Houben-Weyl, Methoden der organischen Chemie (Methods of Organic Chemistry), Volume XV/1 and 2, Stuttgart 1974).

An imino acid is generally understood as meaning natural or unnatural amino acids whose amino group is monosubstituted. In this connection, compounds may particularly be mentioned which can be substituted by $C_1$–$C_8$-alkyl which, in turn, is optionally mono- or diunsaturated and which can be substituted by up to three identical or different radicals from the series comprising mercapto; hydroxyl; $C_1$–$C_7$-alkoxy; carbamoyl; $C_1$–$C_8$-alkanoyl; carboxyl; $C_1$–$C_7$-alkoxycarbonyl; alkoxycarbonyl; F; Cl; Br; I; amino; amidino which can optionally be substituted by one, two or three $C_1$–$C_6$-alkyl radicals; guanidino which can optionally be substituted by one or two benzyloxycarbonyl radicals or by one, two, three or four $C_1$–$C_8$-alkyl radicals; $C_1$–$C_7$-alkylamino; di-$C_1$–$C_7$-alkylamino; $C_1$–$C_6$-alkoxycarbonylamino; $C_7$–$C_{15}$-aralkoxycarbonyl; $C_7$–$C_{15}$-aralkoxycarbonylamino; phenyl-$C_1$–$C_4$-alkoxy; $C_1$–$C_6$-fluorenylmethoxycarbonylamino; $C_1$–$C_6$-alkylsulfonyl; $C_1$–$C_6$-alkylsulfonyl; $C_1$–$C_6$-alkylthio; hydroxamino; hydroximino; sulfamoyl; sulfo; carboxamido; formyl; hydrazono and imino. Suitable heterocycles are also those from the following group: pyrrolidine-2-carboxylic acid, piperidine-2-carboxylic acid, 1,2,3,4-tetrahydroisoquinoline-3-carboxylic acid, decahydroisoquinoline-3-carboxylicacid, octahydroindole-2-carboxylic acid, decahydroquinoline-2-carboxylic acid, octahydrocyclopenta[b]pyrrole-2-carboxylic acid, 2-azabicyclo[2.2.2]octane-3-carboxylic acid, 2-azabicyclo[2.2.1]heptane-3-carboxylic acid, 2-azabicyclo[3.1.0]hexane-3-carboxylic acid, 2-azaspiro[4.4]nonane-3-carboxylic acid, 2-azaspiro[4.5]decane-3-carboxylic acid, spiro[(bicyclo[2.2.1]heptane)-2,3-pyrrolidine-5-carboxylic acid], spiro[(bicyclo[2.2.2]octane)-2,3-pyrrolidine-5-carboxylic acid], 2-azatricyclo[4.3.0.1⁵,⁹]decane-3-carboxylic acid, decahydrocyclohepta[b]pyrrole-2-carboxylic acid, decahydrocycloocta[b]pyrrole-2-carboxylic acid, octahydroisoindole-1-carboxylic acid, 2,3,3a,4,6a-hexahydrocyclopenta[b]pyrrole-2-carboxylic acid, 2,3,3a,4,5,7a-hexahydroindole-2-carboxylic acid, tetrahydrothiazole-4-carboxylic acid, isoxazolidine-3-carboxylic acid, pyrazolidine-3-carboxylic acid, hydroxyproline-2-carboxylic acid, which can all be optionally substituted.

The heterocycles on which the radicals above are based are known, for example, from U.S. Pat. No. 4,344,949, U.S. Pat. No. 4,374,847, U.S. Pat. No. 4,350,703, EP-A 29 488, EP-A 31 741, EP-A 46 953, EP-A 49 605, EP-A 49 658, EP-A 50 800, EP-A 51 020, EP-A 52 870, EP-A 79 022, EP-A 84 164, EP-A 89 637, EP-A 90 341, EP-A 90 362, EP-A 105 102, EP-A 109 020, EP-A 111 873, EP-A 113 880, EP-A 271 865 and EP-A 344 682.

An amino protective group is understood as meaning all amino protective groups customary in peptide chemistry, such as, for example, acetamidomethyl (Acm), 1-adamantyloxycarbonyl (Adoc), 1-(1-adamantyl)-1-methyl-ethoxycarbonyl (Adpoc), allyloxycarbonyl (Aloc), tert.-butyloxycarbonyl (Boc), 1-(4-biphenylyl)-1-methyl-ethoxycarbonyl (Bpoc), α,α-dimethyl-3,5-dimethoxybenzyloxycarbonyl (Ddz), 4-dihydroxaborylbenzyloxycarbonyl (Dobz), 9-fluorenylmethyloxycarbonyl (Fmoc), isobornyloxycarbonyl (Iboc), 1-methylcyclobutyloxycarbonyl (Mboc), 4-methoxybenzyloxycarbonyl (Moc), methylsulfonylethoxycarbonyl (Msc), 2-phosphonioethoxycarbonyl (Peoc), phenylsulfonylethoxycarbonyl (Pse), 4-pyridylmethoxycarbonyl (Pyoc), 2,2,2-trichloro-tert.-butyloxycarbonyl (Tcboc), toluolsulfonylethoxycarbonyl (Tse), benzyloxycarbonyl (Z), halogen-substituted benzyloxycarbonyl (Z(Hal$_n$)), 4-nitro-benzyloxycarbonyl (Z(NO$_2$)) (see also, for example, T. W. Greene, "Protective Groups in Organic Chemistry", New York, John Wiley & Sons, 1981; A. Hubbuch, Kontakte Merck 1979, No. 3, pages 14–23). Fmoc, Boc and Z are preferred. Third functions of the amino or imino acids can be protected by suitable protective groups, such as are described, for example, in E. E. Büllesbach, Kontakte Merck 1980, No. 1, pages 23–35, or glycosylated (see, for example, EP-A 263 521 (HOE 86/F 253)). The following may be mentioned in particular: Arg(Tos), Arg(Mts), Arg(Mtr), Arg(Pmc), Asp(OBzl), Asp(OtBu), Cys(4-MeBzl), Cys(Acm), Cys(StBu), Glu(OBzl), Glu(OtBu), His(Tos), His(Fmoc), His(Dnp), His(Trt), Lys(Cl-2), Lys(Boc), Met(O), Ser(Bzl), Ser(tBu), Thr(Bzl), Thr(tBu).

$C_6$–$C_{14}$-Aryl is, for example, phenyl, naphthyl, biphenylyl or fluorenyl; phenyl and naphthyl are preferred. $C_5$–$C_{12}$-heteroaryl is understood as meaning mono-, bi- or tricyclic heteroaromatics which do not contain an acidic —NH group. Examples which may be mentioned are: pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl or β-carbolinyl.

The alkylated peptides can be purified by crystallization or by silica gel chromatography. When using triphenylphosphine, the triphenylphosphine oxide formed in the reaction is often poorly separable. This problem does not occur with water-soluble triarylphosphines—such as, for example, p-dimethylaminodiphenylphosphine. The phosphine oxide derivative formed here is very easily separated off from lipophilic compounds—for example protected alkylated peptides—since it is readily soluble in acidic aqueous medium (M. von Itzstein et al., Synth. Comm. 1990, 20, 2049). However, triphenylphosphine oxide can also be separated off by removing the amino protective group and then readily separating off the water-soluble salts of the resulting peptides from the lipophilic triphenylphosphine oxide by partition between water and ethyl acetate or ether. If polymer-bound triphenylphosphine is used, the triphenylphosphine oxide derivative formed can be separated off by filtration. When using tri-n-butylphosphine (PBu$_3$), it was found that this reagent is not compatible with the Fmoc protective group. The amino protective group mentioned is partially removed during the reaction, so that in this case a base-stable protective group (such as, for example, the Boc group) should be used.

Starting Material a) Fmoc-Phe-Azagly-NH$_2$ (C$_{25}$H$_{24}$N$_4$O$_4$, MW 444)

5.43 g (1 eq.) of HOBt, 4.32 g (1 eq.) of semicarbazide HCl and 4.90 ml (1 eq.) of NAM are added to a solution of 15 g (38.76 mmol) of Fmoc-Phe-OH in 70 ml of DMF. The mixture is cooled to 0° C. and 8.14 g (1 eq.) of DCC is added with stirring. The mixture is stirred for one hour at 0° C. and the solution is allowed to stand overnight. The solution is then filtered and concentrated in a rotary evaporator. The residue is partitioned between AcOEt/water. The peptide precipitates during extraction by shaking. The precipitate is filtered off with suction and washed liberally with water and then with ether and dried in a high vacuum. 13.10 g (29.50 mmol) of peptide are obtained. The mother liquor (AcOEt phase) is treated in the usual way (washing with saturated NaHCO$_3$ solution (twice), water, KHSO$_4$ solution, water, and drying over sodium sulfate). The organic phase is concentrated in a rotary evaporator, and the precipitate is triturated with ether and filtered off on a suction filter. It is then dried in a high vacuum. A further 0.92 g (2 mmol) of peptide is obtained.

Yield: 14.02 g (31.57 mmol) = 81%

M.p.: 193° C.

$[\alpha]_D^{23}$: −16.2° (c=1 in AcOH)

b) Boc-Phe-Azagly-NH$_2$ (C$_{15}$H$_{22}$N$_4$O$_4$, MW 322)

15.85 g (1 eq.) of HOBt, 12.61 g (1 eq.) of semicarbazide HCl and 14.33 ml (1 eq.) of NAM are added to a solution of 30 g (113.2 mmol) of Boc-Phe-OH in 100 ml of DMF. The mixture is cooled to 0° C. and 23.77 g (1 eq.) of DCC are added with stirring. The mixture is stirred for a further hour and stood over the weekend. The solution is then filtered and concentrated in a rotary evaporator. The residue is partitioned between AcOEt and water, and the organic phase is washed successively with saturated NaHCO$_3$ solution (3 times), water, KHSO$_4$ solution (twice) and water. After drying, the solution is concentrated on a rotary evaporator, and the residue is triturated with ether, filtered off on a suction filter and dried in a high vacuum.

Yield: 20.31 g (63 mmol) = 57%

$[\alpha]_D^{23}$: 2.2° (c=1 in AcOH)

EXAMPLE 1 a) Fmoc-Phe-N(Me)-NH-CONH$_2$ (C$_{26}$H$_6$N$_4$O$_4$, MW 458)

2.5 g (5.63 retool) of Fmoc-Phe-Azagly-NH$_2$ as a suspension, 1.83 ml (8 eq.) of MeOH, 2.96 g (2 eq.) of triphenylphosphine (PPh$_3$), 1.773 ml (2 eq.) of diethyl azodicarboxylate (DEAD) in portions and, after stirring for 15 min., a further 738 mg (0.5 eq.) of PPh$_3$ and 0.443 ml (0.5 eq.) of DEAD are added, at 0° C., to 50 ml of absolute THF. PPh$_3$ and DEAD are again added in the same amount after a further 15 min. This suspension is then placed at RT and stirred for 4 hours (no longer any starting material!). This suspension is filtered, and the precipitate is washed with ether and dried in a high vacuum. 930 mg (2.03 mmol) of pure N-Me derivative (36%) are obtained. The mother liquor is then concentrated in a rotary evaporator, and the residue is triturated with ether and filtered off with suction. This precipitate contains the desired compound and triphenylphosphine oxide (POPh$_3$).

M.p.: 173°–174° C.

$[\alpha]_D^{23} = +27°$ (c=1 in AcOH)

b) HCl-Phe-N(Me)-NH-CONH$_2$ (C$_{11}$H$_{16}$N$_4$O$_2$, MW 236)

900 mg (1.96 mmol) of pure Fmoc-Phe-N(Me)-NH-CONH$_2$ are dissolved in 15 ml of DMF. 2.16 ml (10 eq.) of Et$_2$NH are then added to this. The mixture is stirred for 15 min. and the solution is concentrated in a rotary evaporator. The residue is triturated with ether and filtered off on a suction filter. The compound is then dissolved in MeOH, and the solution is brought to pH 6.40 with 1N HCl and concentrated in a rotary evaporator. The residue is triturated with ether, filtered off on a suction filter and dried in a high vacuum.

Yield: 430 mg (1.58 mmol)=80%
M.p.: 98°–105° C.
$[\alpha]_D^{23} = +23°$ C. (c=1 in AcOH)

EXAMPLE 2 a) Fmoc-Phe-N (Et) -NH-CONH$_2$ (C$_{27}$H$_{28}$N$_4$O$_4$, MW 472)

4 g (9 retool) of Fmoc-Phe-Azagly-NH$_2$ as a suspension, 4.23 ml (8 eq.) of EtOH, 4.72 g (2 eq.) of PPh$_3$ and 2.834 ml (2 eq.) of DEAD are added to 50 ml of absolute THF. In the course of 15 min., 0.5 eq. of PPh$_3$ (1.18 g) and DEAD (0.708 ml) are again added a further two times. After the second addition, the suspension is stirred for 4 hours. The solution is then concentrated in a rotary evaporator and the compound is purified by silica gel chromatography (eluent: CH$_2$Cl$_2$/AcOEt=9/1 and CH$_2$C$_2$/MeOH=9.5: 0.5). The fractions (contaminated with POPh$_3$) are concentrated in a rotary evaporator and the residue is triturated with petroleum ether (PE), filtered on a suction filter and dried in a high vacuum.

b) HCl-Phe-N(Et)-NH-CONH$_2$ (C$_{12}$H$_{18}$N$_4$O$_2$, MW 250)

9 mmol of the peptide obtained above (containing POPh$_3$; calculated as 100% yield) is dissolved in 20 ml of DMF. After addition of 9.90 ml (10 eq.) of Et$_2$NH, the mixture is stirred for 30 min. and the solution is concentrated in a rotary evaporator. The residue is triturated twice with PE, then suspended in a mixture of AcOEt/water and brought to pH 6.40 with stirring using 1N HCl. This mixture is then extracted by shaking, and the water phase is washed 3 times with ether, concentrated somewhat in a rotary evaporator (remainder of ether and AcOEt distilled off), filtered and freeze-dried.

Yield: 1.42 g (5.68 mmol)=56%
M.p.: 91°–94° C.
$[\alpha]_D^{23} = +62.5°$ (c=1 in AcOH).

EXAMPLE 3 a) Fmoc-Phe-N(iPr)-NH-CONH$_2$ (C$_{28}$H$_{30}$N$_4$O$_4$, MW 486)

The title compound is prepared analogously to Example 2a.
Reagents:
Fmoc-Phe-Azagly-NH$_2$: 4g, 9 mmol
iPrOH: 5.50 ml (8 eq.)
PPh$_3$: 4.72 g (2 eq.)
DEAD: 2.834 ml (2 eq.)
1.18 g .of PPh$_3$ (0.5 eq.) and 0.708 ml of DEAD (0.5 eq.) twice After 4 hours, the solution is concentrated in a rotary evaporator and the peptide is purified by silica gel chromatography (eluents: CH$_2$Cl$_2$/AcOEt=9:1 and CH$_2$Cl$_2$/MeOH=9:1). The fractions (peptides containing POPh$_3$) are concentrated in a rotary evaporator, and the residue is triturated with PE, filtered off on a suction filter and dried in a high vacuum.

b) HCl -Phe-N(iPr)-NH-CONH$_2$ (C$_{13}$H$_{20}$N$_4$O$_2$, MW 264)

Batch of 9 retool; analogously to Example 2b.
Yield: 1.48 g (5.60 retool)=55%
M.p.: 105°–110° C.

EXAMPLE 4 a) Boc-Phe-N(CH$_2$(2-pyridyl))-NH-CONH$_2$ (C$_{21}$H$_{27}$N$_5$O$_4$, MW 413)

4 g (12.42 retool) of Boc-Phe-Azagly-NH$_2$, 4.80 ml (2 eq.) of 2-pyridylmethanol, 6.51 g (2 eq.) of PPh$_3$, 3.911 ml (2 eq.) of DEAD and, in the course of 15 min., 1.63 g (0.5 eq.) of PPh$_3$ and 0.978 ml (0.5 eq.) of DEAD a further two times are added to 50 ml of absolute THF at 0° C. The solution is stirred for two hours at 0° C. and for two hours at RT. The solution is then concentrated in a rotary evaporator, and the residue is partitioned between ether and water and rapidly separated off. The organic phase is allowed to stand at 0° C. for 30 min. The precipitate is then filtered off on a suction filter, washed with cold ether and dried in a high vacuum. 1.41 g (3.41 retool) of pure compound are obtained. The mother liquor is concentrated in a rotary evaporator and triturated with water until a solid substance is obtained. This precipitate is then taken up in CH$_2$Cl$_2$, and the solution is dried and concentrated in a rotary evaporator. This fraction is purified by silica gel chromatography (eluent CH$_2$Cl$_2$/MeOH=9:0.4, then CH$_2$Cl$_2$/MeOH =9:1). 370 mg .(0.89 mmol) of pure substance are obtained.

Yield: 1.78 g=35%
$[\alpha]_D^{23}$: +8.9° (c=1 in AcOH)

b) 2 HCl-Phe-N(CH$_2$-(2-pyridyl))-NH-CONH$_2$ (C$_{16}$H$_{19}$N$_5$O$_2$, MW 313)

1.69 g (4.09 mmol) of pure Boc-Phe-N(CH$_2$-(2-pyridyl))-NH-CONH$_2$ are suspended in 20 ml of dioxane. 20 ml of saturated HCl-dioxane solution are added to this at 0° C. and the mixture is stirred at 0° C. for one hour. The solution is then concentrated in a rotary evaporator, the residue is partitioned between AcOEt and water and the water phase is washed a further two times with AcOEt. The water phase is then concentrated somewhat in a rotary evaporator, filtered and freeze-dried.

Yield: 1.29 g (3.34 mmol)=84%

EXAMPLE 5 a) Boc-Phe-N(CH$_2$-(2-naphthyl))-NH-CONH$_2$ (C$_{26}$H$_{30}$N$_4$O$_4$, MW 462)

4 g (12.42 mmol) of Boc-Phe-Azagly-NH$_2$, 2.17 g (1.1 eq.) of 2-naphthalenemethanol, 6.19 ml (2 eq.) of PBu$_3$ and 3.911 ml (2 eq.) of DEAD are added at 0° C. to 50 ml of absolute THF. This solution is stirred for 2 hours at 0° C. and for a further 2 hours at RT. The solution is then concentrated in a rotary evaporator, the residue is triturated with 100 ml of PE and this mixture is stirred at 0° C. for 5 min. 10 to 20 ml of ether are added and a white precipitate is then obtained and is filtered off on a suction filter. The precipitate is dried in a high vacuum.

3.14 g of peptide derivative (contaminated with POBu$_3$) are obtained. The mother liquor is concentrated in a rotary evaporator and allowed to stand in a cold room over the weekend in PE. The precipitate is then filtered off with suction, washed with cold PE and dried in a high vacuum. A further 1.40 g of crude peptide (peptide containing POBu$_3$) is obtained. This second fraction is then purified by silica gel chromatography (eluent: CH$_2$Cl$_2$/MeOH=9:0.5). The fractions are concentrated in a rotary evaporator, and the residue is triturated with PE, filtered off on a suction filter and dried in a high vacuum.

Yield: 520 mg
$[\alpha]_D^{23}$: +40.1° (c=1 in AcOH)

b) HCl -Phe-N (CH$_2$-(2-naphthyl))-NH-CONH$_2$
(C$_{22}$H$_{22}$N$_4$O$_2$, MW 362)

500 mg (1.08 mmol) of pure Boe-Phe-N(CH$_2$-(2-naphthyl))-NH-CONH$_2$ are dissolved in 10 ml of dioxane. 10 ml of a saturated HCl-dioxane solution are added to this at 0° C. with stirring and the mixture is stirred for a further hour at 0° C. The solution is then concentrated in a rotary evaporator, and the residue is triturated with ether, filtered off on a suction filter and dried in a high vacuum.

Yield: 360 mg (0.90 mmol)=90%

EXAMPLE 6 a) Z-Tyr(OiPr)-Pro-N(iPr)-NH-CONH$_2$ (C$_{29}$N$_{39}$N$_5$O$_6$, MW 553)

The title compound is prepared analogously to Example 2a.

Reagents:
Z-Tyr-Pro-Azagly-NH$_2$: 5 g (10 mmol)
iPrOH: 5.80 ml (7.5 eq.)
PPh$_3$:5.25 (2 eq.)
DEAD: 3.15 ml (2 eq.)
1.31 g of PPh$_3$ (0.5 eq.) and 0.80 ml of DEAD (0.5 eq.) twice After 4 hours, the solution is concentrated in a rotary evaporator and the residue is purified by silica gel chromatography (eluents: 1) CH$_2$Cl$_2$/Acetone=9: 1 and 2) CH$_2$Cl$_2$/MeOH=9.5: 0.5). The fractions are concentrated in a rotary evaporator, and the residue is triturated with PE, filtered off on a suction filter and dried in a high vacuum.

Yield: 4.46 g (8.06 mmol)=80%
$[\alpha]_D^{23}$: −23.5° (c=1 in AcOH)

List of the abbreviations used:
Cha: cyclohexylalanine
Chg: cyclohexylglycine
DCC: dicyclohexylcarbodiimide
DMF: dimethylformamide
Nal: 3-(2-naphthyl)alanine
NAM: N-acetylmorpholine
Npg: neopentylglycine
PE: petroleum ether
Tbg: tert.-butylglycine
Thia: 2-thienylalanine

We claim:

1. A process for the preparation of an alkylated azaglycine derivative of the formula I $$X—(A)_n—N(R)—NH—CO—NH_2 \qquad (I)$$

in which

X is an amino protective group wherein said protective group is Fmoc, Boc or Z; or X is C$_1$-C$_8$-alkanoyl, C$_6$-C$_{14}$-arylcarbonyl or C$_6$-C$_{14}$-aryl-C$_1$-C$_4$-alkanoyl;

A is an α-amino acid or an α-amino acid radical whose amino group is monosubstituted, on the third function, when present, A is optionally protected;

n is 0–10, X being C$_1$-C$_8$-alkanoyl, C$_6$-C$_{14}$-arylcarbonyl or C$_6$-C$_{14}$-aryl-C$_1$-C$_4$-alkanoyl if n=0; and R is C$_1$-C$_{18}$-alkyl, C$_6$-C$_{14}$-aryl-C$_1$-C$_4$-alkyl, C$_5$-C$_7$-heteroaryl, or pyridyl C$_1$-C$_4$-alkyl wherein heteroaryl does not contain an acidic-NH group, and wherein said C$_6$-C$_{14}$-aryl-C$_1$-C$_4$-alkyl, C$_5$-C$_7$-heteroaryl, or pyridyl C$_1$-C$_4$-alkyl are optionally substituted in the aromatic ring by a halogen, a C$_1$-C$_6$ alkyl or a C$_1$-C$_6$ alkoxy;

which comprises reacting a compound of the formula II $$X—(A)_n—NH—NH—CO—NH_2 \qquad (II)$$

in which X, A and n have the above mentioned meanings, with a primary or secondary C$_1$-C$_{18}$-alkylalkanol, a C$_6$-C$_{14}$-aryl-C$_1$-C$_4$-alkanol, a C$_5$-C$_7$-heteroaryl alcohol or a pyridyl C$_1$-C$_4$ alkanol, wherein said heteroaryl does not contain an acetic-NH group and wherein said C$_6$-C$_{14}$ aryl-C$_1$-C$_4$ alkanol, C$_5$-C$_7$ heteroaryl alcohol and pyridyl C$_1$-C$_4$ alkanol are optionally substituted in the aromatic ring by a halogen, a C$_1$-C$_6$ alkyl or a C$_1$-C$_6$ alkoxy, and excess DEAR, and a tri-C$_1$-C$_6$-alkylphosphine, tri-C$_6$-C$_{14}$-arylphosphine or pyridyl-di-C$_6$-C$_{14}$-arylphosphine, it being possible for the aryl moiety to be optionally substituted by di-C$_1$-C$_4$-alkylamino, in an ether at 0° C. to 30° C., and removing the amino protective group X, with the proviso that X is not Fmoc when tri-n-butylphosphine is used.

2. A process as claimed in claim 1, wherein triphenylphosphine, tri-n-butylphosphine, p-dimethylaminophenyldiphenylphosphine, pyridyldiphenylphosphine or polymer-bound triphenylphosphine is used.

* * * * *

UNITED STATES PATENT AND TRADEMARK OFFICE
CERTIFICATE OF CORRECTION

PATENT NO. : 5,326,875
DATED : July 5, 1994
INVENTOR(S) : Patrice Talaga et al.

It is certified that error appears in the above-indentified patent and that said Letters Patent is hereby corrected as shown below:

Claim 1, column 8, line 43, change "DEAR" to --DEAD--.

Signed and Sealed this

Seventh Day of February, 1995

BRUCE LEHMAN

*Attest:*

*Attesting Officer*     *Commissioner of Patents and Trademarks*